United States Patent [19]

Numazawa et al.

[11] 4,416,658
[45] Nov. 22, 1983

[54] BLOOD SUCTION DEVICE

[75] Inventors: Masaaki Numazawa, Kamakura; Hidetaka Tashiro, Hadano; Shuichi Ishii, Yokohama, all of Japan

[73] Assignee: Senko Medical Instrument Mfg. Co., Tokyo, Japan

[21] Appl. No.: 314,027

[22] Filed: Oct. 22, 1981

[30] Foreign Application Priority Data

Oct. 30, 1980 [JP] Japan ................................ 55-152867
Oct. 30, 1980 [JP] Japan ................................ 55-155577

[51] Int. Cl.³ .......................................... A61M 31/00
[52] U.S. Cl. ...................................... 604/48; 604/902; 433/100
[58] Field of Search ............................ 433/27, 84, 100; 200/832, 81.9 R; 128/276, 348, 349 R, 350 R, 766, 303 R; 604/902, 48, 52, 53-55, 289

[56] References Cited

U.S. PATENT DOCUMENTS

| 2,604,685 | 7/1952 | Harms | 128/276 |
| 3,191,600 | 6/1965 | Everett | 604/902 |
| 3,494,363 | 2/1970 | Jackson | 128/303.17 |
| 4,180,074 | 12/1979 | Murry et al. | 128/276 |
| 4,209,678 | 6/1980 | Hussey | 200/832 |

Primary Examiner—Richard J. Apley
Assistant Examiner—J. L. Kruter
Attorney, Agent, or Firm—Darby & Darby

[57] ABSTRACT

A blood suction device for removing blood from a surgical field is provided which can be controlled by a pressure sensing means mounted on a suction tip of the device for starting and stopping the roller pump of the device, and changing the revolution rate of the roller pump, thus enabling to reduce possible hemolysis, clothing and other undesirable effects. The blood suction device comprises pressure sensing means for detecting the pressure exerted thereupon which can be handled adjacent the suction tip by means of pneumatic pressure, and control means for controlling the revolution rate in response to the sensed pressure. The revolution rate when the device is not gripped or pushed by the operator may be set either at zero revolution or at any desired revolution.

4 Claims, 4 Drawing Figures

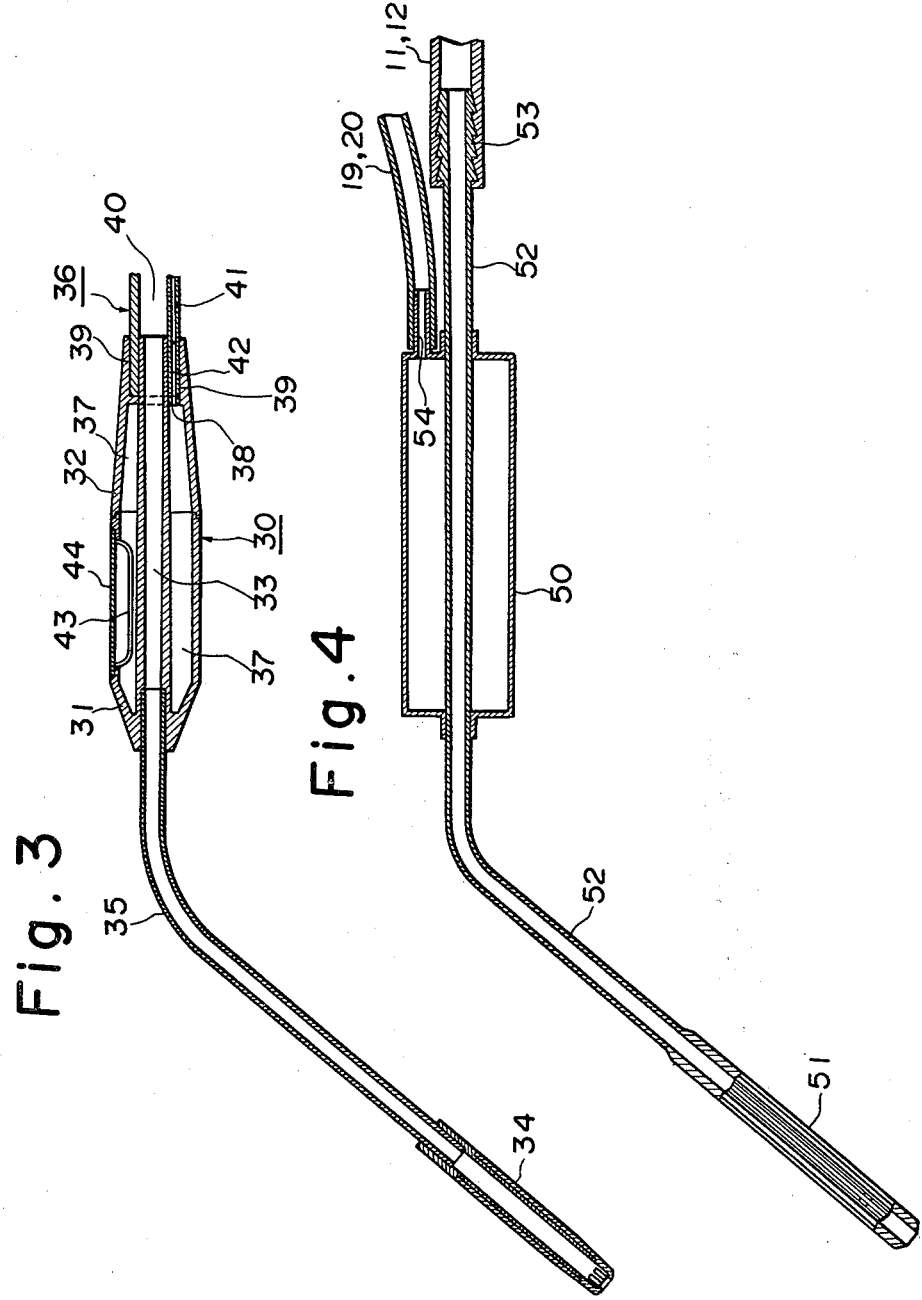

BLOOD SUCTION DEVICE

BACKGROUND OF THE INVENTION

1. Field of the Invention

The present invention relates to a blood suction device which is used at a surgical site for drainage of pooled blood in order to keep the operating field clear of blood and thus visible to the surgeon, and in which hemolysis, infection, clotting and other undesirable effects upon blood can fully be eliminated.

2. Description of the Prior Art

Blood suction devices are extensively used in such medical procedures as cardiotomy operations for keeping the operating field clear of blood and thus visible to the surgion, and the sucked blood is usually re-infused to the patient during or after the operation. The known blood suction device has a suction tip and a roller pump communicating with the tip by a length of flexible tubing through which blood is conveyed. The roller pump is commonly positioned remotely from the surgical field at a pump-oxygenator which is used for controlling circulation and oxygenation of the blood bypassed from the heart. A typical perfusion system is shown in FIG. 1 in order to more fully understand the present invention. The venous return from ascending and descending vena cava is introduced to an oxygenator 1 through tubes 2, 3 by means of gravity venous drainage. The blood is oxygenated at the oxygenator 1 and then re-infused to an aorta and a femoral artery through pumping tubes 4, 5 which are subjected to occlusion by means of a roller pump 6. The blood which may accumulate within the heart is removed by venting thereof by means of a roller pump 7 and then is conveyed through a cardiotomy return reservoir 8 to the oxygenator 1, and also is re-infused to the aorta and the femoral artery. The pump-oxygenator units are used in many of the major surgical procedures in which a blood suction device is essential for keeping the operating field clear of blood and visible to the surgeon. Thus, conventionally one or more, illustratively two in FIG. 1, of the blood suction devices are used in the perfusion system.

Each of the known blood suction devices comprises respectively suction tips 9, 10, pumping tubes 11, 12 communicating with the suction tips 9, 10 for drainage of the pooled blood, and roller pumps 13, 14 engaging with the pumping tubes 11, 12 for occlusion thereof. The ends of the pumping tubes 11, 12 are connected to the cardiotomy return reservoir 8 so that the blood may be re-infused in a similar manner as described above to the patient during or after the operation. These conventional blood suction devices have been found not entirely satisfactory, however, in that, since the surgical field is positioned remotely from the pump-oxygenator unit and other associated devices where the control of the blood suction devices are managed, the instructions given by the surgeon handling the blood suction tip at the surgical field can not reach the already overburdened pump technician in sufficient time for him to control the blood suction devices immediately. The time lag between the instructions and the real initiation of the control may cause the blood suction device to suck air which results in an increase of blood hemolysis, or may cause the blood suction device to suck blood too slowly to attain the drainage of the large amount of pooled blood in a short time. Thus, when the roller pumps 13, 14 operate without the suction tips 9, 10 being immersed in blood, a rush of air through the pumping tubes 11, 12 is generated so that a great deal of hemolysis, as well as clotting and other undesirable effects may occur.

SUMMARY OF THE INVENTION

It is therefore a principal object to provide a new and improved blood suction device which can be controlled by a pressure sensing means mounted on a suction tip for starting and stopping the roller pump, and changing the revolution rate of the roller pump.

It is a further object to provide a blood suction device as described above which is easy in handling and moreover can be implemented without the use of electrical components near the surgical field and with the use of disposable components for preventing possible infection.

According to the invention, there is provided a blood suction device for removing blood from a surgical incision comprising: a suction tip made of a tubular member forming a blood conduit along the entire length thereof for sucking blood; a pumping tube communicating at one end thereof with the suction tip and at the other end thereof with a blood reservoir; a roller pump driven by a motor and positioned between the one and the other end of the pumping tube for actuating thereupon to convey the blood from the suction tip to the reservoir; pressure sensing means mounted on the suction tip for sensing a pressure exerted thereupon, the pressure sensing means having an outlet to which one end of a pressure conduit is connected; and control means positioned remotely from the suction tip for converting the sensed pressure at the other end of the pressure conduit into an electrical signal and generating a control signal for driving the motor, the control signal causing the motor to revolve at an increased or decreased revolution rate in response to the sensed pressure, and when no pressure is sensed with the pressure sensing means, to revolve at a predetermined revolution rate including zero revolution.

According to one aspect of the present invention, it is preferably that the pressure sensing means comprises front and rear grip members which are made of relatively rigid synthetic resin and are coupled with each other to form centrally and along the entire length thereof a coupling conduit which communicates with the suction tip and the pumping tube, and to form around and outward the coupling conduit an empty space, the rear grip member having at the rear end and around the coupling conduit a cylindrical groove, at the bottom of which the outlet is formed to communicate with the empty space, the front grip having an opening which communicates with the empty space and a resilient membrane being secured to the opening for transmission of the pressure exerted thereupon to the outlet. A double lumen pipe inserted into the cylindrical groove is used as a part of the pressure conduit and the pumping tube.

BRIEF DESCRIPTION OF THE DRAWINGS

In the drawings,

FIG. 3 is a sectional view of a first embodiment of a blood suction device according to the present invention, and FIG. 4 is a sectional embodiment of a blood suction device according to the present invention.

DETAILED DESCRIPTION OF THE PREFERRED EMBODIMENT

The invention will now be described in more detail with reference to the accompanying drawings.

Figure 1:
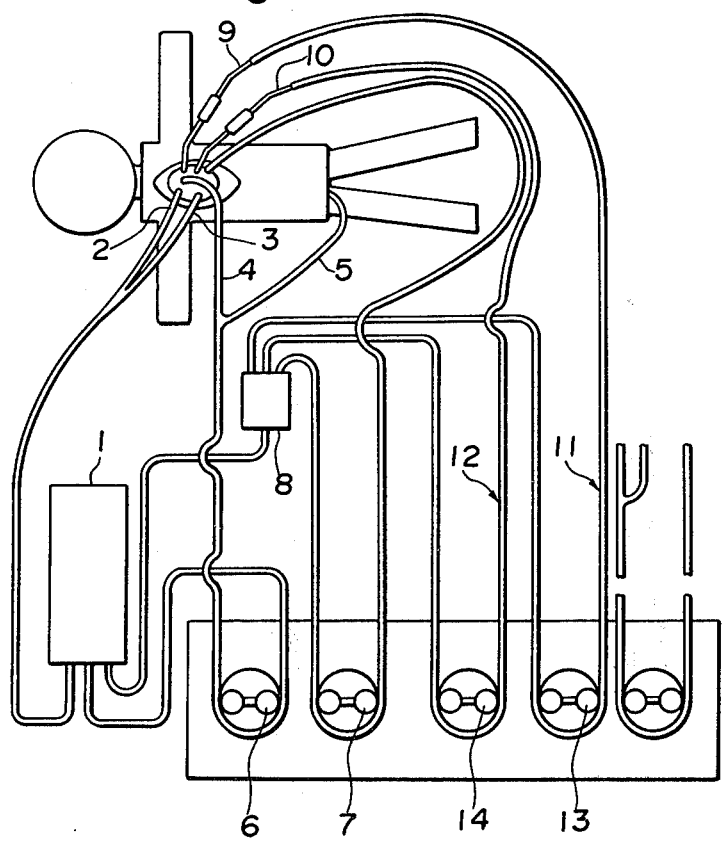
FIG. 1 is a schematic diagram showing a typical perfusion system in which a blood suction device according to the prior art is employed.
Figure 2:
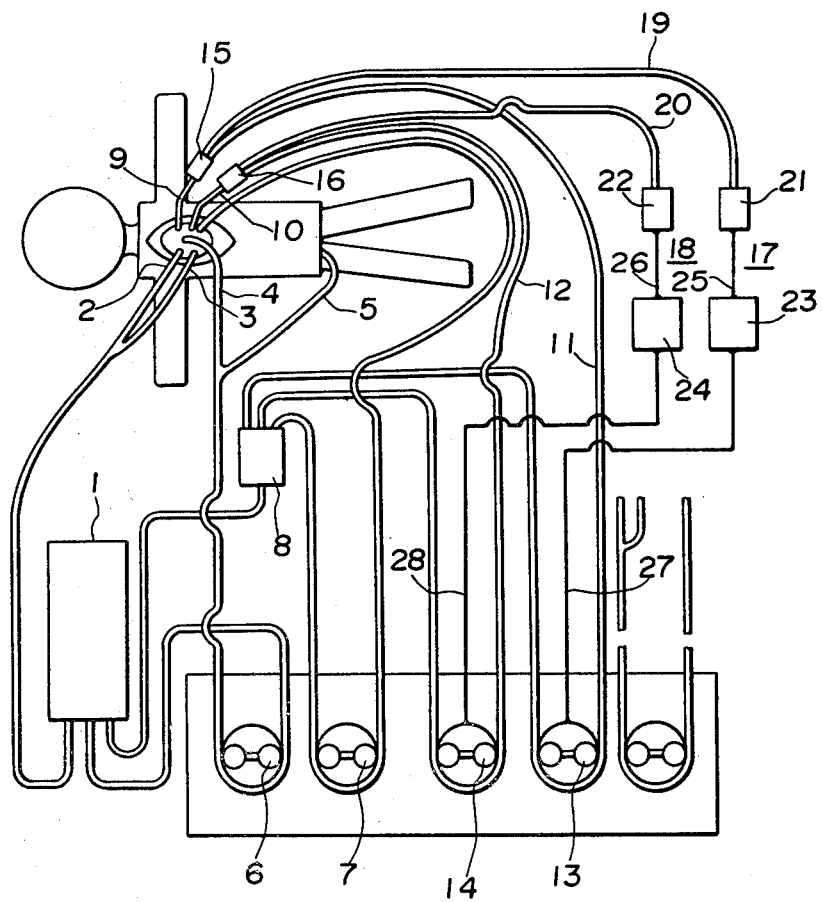
FIG. 2 is a schematic diagram showing a perfusion system wherein a blood suction device according to the present invention is employed.

FIG. 2 shows a schematic diagram illustrating a perfusion system in which blood suction devices according to the present invention are applied. In the drawing most of the parts are identical with those in FIG. 1 and thus have identical reference numerals. The detailed description of these identical structures is omitted herein for the purpose of brevity. In FIG. 2 new and improved blood suction devices are employed in the perfusion system. In this illustrative example, two blood suction devices are used and each comprises respectively blood suction tip 9, 10 pumping tube 11, 12 communicating with the suction tip 9, 10 for drainage of the pooled blood, and roller pump 13, 14 engaging with the pumping tube 11, 12 for occlusion thereof. The roller pumps 13, 14 are driven by respective motors not shown in a conventional manner. In addition to the above known construction, the blood suction device according to the present invention further comprises, in the illustrative example, respectively pressure sensing means 15, 16 and control means generally designated at 17, 18.

The pressure sensing means 15, 16, which are described in detail hereafter with reference to FIG. 3 and 4, are mounted on the respective suction tips 9, 10 for sensing pressures exerted thereupon when an operator grips the pressure sensing means 15, 16. The pressure sensing means 15, 16 have respectively outlets to which respective one end of pressure conduits 19, 20 are connected.

The control means 17, 18 comprise respectively pressure transducers 21, 22 and control circuit 23, 24. The pressure transducers 21, 22 are connected to the other end of the pressure conduits 19, 20 and convert the sensed pressures into electrical signals and in turn output control signals to the respective control circuits 23, 24 via lines 25, 26. The pressure transducers 21, 22 may be of a type known as strain gauges or the like. The control circuits 23, 24 receive via lines 27, 28 the control signals from the pressure transducers 21, 22 and control the motors in proportion to the magnitudes of the control signals so that the roller pumps 13, 14 are driven to respective revolution rates which are proportional to the magnitudes of the control signals and hence to the pressures exerted on the respective pressure sensing means 15, 16. When no pressure is applied to the respective pressure sensing means 15, 16, it is preferable to set the revolution rates of the roller pumps 13, 14 at predetermined revolution rates including illustratively zero to 50 revolution per minute. Setting thus the revolution rates when no pressure is applied, it is possible either to stop the roller pumps 13, 14 or to revolve them at predetermined revolution rates when the operator does not grip the pressure sensing means. As a result the operator can engage with other services without paying attention to the blood suction devices. It is also to be noted that the control means 17, 18 are positioned remotely from the suction tips 9, 10 or the surgical field by means of the pressure conduits 19, 20, so that protection against leakage of electrical current are assured in the vicinity of the surgical field.

Referring now to FIGS. 3 and 4, preferred embodiments of the pressure sensing means are shown. The embodiment of FIG. 3 is characterized in that its grip portion is formed relatively rigid, and a pressure conduit and pumping tube are integrally formed in a double lumen pipe, while the embodiment of FIG. 4 is characterized in that it is formed as a whole a flexible squeeze bulb.

In FIG. 3, a pressure sensing means generally designated at reference numeral 30, is composed of mainly a front grip 31 and a rear grip 32 which are made of relatively rigid synthetic resin. The front and rear grips 31, 32 are adapted to couple together so that a coupling conduit 33 is formed centrally and along the entire length of the coupled front and rear grips 31, 32. The coupling conduit 33 communicates at one end with a suction tip 34 via an elongated pipe 35 which is connected to the front grip 31, and at the other end with one lumen of a double lumen pipe 36. An empty space 37 is also formed around and outward the coupling conduit 33. A cylindrical groove 39 is formed at the rear end of the rear grip 32 outward of the coupling conduit 33, an outlet 38 which communicates with the empty space being formed at the bottom of the cylindrical groove 39. The double lumen pipe 36 has a larger lumen 40 communicating with the coupling conduit 33 and a smaller lumen 41 communicating with the outlet 38. The smaller lumen 41 has a stainless steel tube 42 inserted therein at the region where the cylindrical groove 39 extends, so that a smooth passageway can be obtained without fear of being crushed or obstructed by adhesive agents which fix the double lumen pipe 36 to the cylindrical groove 39. An opening 43 is formed at the outer surface of the front grip 31 for communication with the empty space 37, a resilient membrane 44 being secured to the opening 43 for transmission of the pressure exerted thereupon to the outlet 38.

The double lumen pipe 36 is used only at a portion adjacent the rear grip 32 substituting for the pressure conduit 19 or 20 and the pumping tube 11 or 12, and at the other portion remote from the rear grip 32 the independent pressure conduit 19 or 20 and pumping tube 11 or 12 are used, each respectively for coupling to the pressure transducer 21 or 22 and for engaging with the roller pump 13 or 14.

Referring to FIG. 4, another embodiment of the pressure sensing means is shown in which a squeeze bulb made of synthetic resin or rubber material is designated by reference numeral 50. A suction tip 51 with an elongated pipe 52 is used for coupling to the pumping tube 11 or 12 by means of a tube connector 53. The squeeze bulb 50 is mounted on the elongated pipe 52 and has an outlet 54 which communicates with the squeeze bulb 50 for transmitting the pressure exerted thereupon to the pressure conduit 19 or 20.

As described previously, the pressure sensing means 30, 50 deliver the pressures, when the resilient membrane 44 or the squeeze bulb 50 is pushed by an operator, to the respective outlets 38, 54 and to the respective pressure conduits 19, 20, so that the pressure transducers 21, 22 sense the pressures to output the control signals to the control circuits 23, 24. Thus, the control circuits 23, 24 control the roller pump 13, 14 to revolve in proportion to the magnitudes of the sensed pressures. Contrary to the above, when the resilient membrane 44 or the squeeze bulb 50 is maintained untouched by the operator, the roller pump 13, 14 operates at predetermined revolution rates including zero revolution so that the operator can select either to stop the roller pump 13, 14 or to drive it at the predetermined revolution rates when the operator does not touch the resilient member 44 or the squeeze bulb 50.

Thus, according to the present invention, the blood suction device can be controlled by a pressure sensing means mounted on a suction tip so that quick and precise control of the blood suction can be obtained to reduce hemolysis, as well as clotting and other undesirable effects. Moreover, the blood suction device according to the invention is easy in handling and can be implemented without the use of electrical components near the surgical fields and with the use of disposable components for preventing possible infection.

As various changes may be made in the form, construction and arrangement of the parts herein, without departing from the spirit and scope of the invention and without sacrificing any of its advantages, it is to be understood that all matter herein is to be interpreted as illustrative and not in any limiting sense.

What is claimed is:

1. A blood suction device for removing blood from a surgical field comprising:
   a suction tip of a type used in cardiotomy operations made of a tubular member forming a blood conduit along the entire length thereof for sucking the blood;
   a pumping tube communicating at one end thereof with said suction tip and at the other end thereof with a blood reservoir;
   a roller pump of a type used in cardiotomy operations driven by a motor and positioned between said one and the other end of said pumping tube for acting thereupon to convey the blood from said suction tip to said reservoir;
   pressure sensing means mounted on said suction tip for sensing a pressure exerted thereon, said pressure sensing means having an outlet to which one end of a pressure conduit is connected; and
   control means positioned remotely from said suction tip for converting said sensed pressure at the other end of said pressure conduit into an electrical signal and generating a control signal for driving said motor, said control signal causing said motor to revolve at an increased or decreased revolution rate in response to said sensed pressure, and when no pressure is sensed with said pressure sensing means, to revolve at a predetermined revolution rate including zero revolution.

2. A blood suction device according to claim 1, wherein said pressure sensing means is a squeeze bulb of substantially a hollow sleeve shape mounted lengthwise on said suction tip, said pressure sensing means being made of synthetic resin and resilient so as to sense the pressure exerted thereupon.

3. A blood suction device for removing blood from a surgical field comprising:
   a suction tip made of a tubular member forming a blood conduit along the entire length thereof for sucking the blood;
   a pumping tube communicating at one end thereof with said suction tip and at the other end thereof with a blood reservoir;
   a roller pump driven by a motor and positioned between said one and the other end of said pumping tube for acting thereupon to convey the blood from said suction tip to said reservoir;
   pressure sensing means mounted on said suction tip for sensing a pressure exerted thereon, said pressure sensing means having an outlet to which one end of a pressure conduit is connected; and
   control means positioned remotely from said suction tip for converting said sensed pressure at the other end of said pressure conduit into an electrical signal and generating a control signal for driving said motor, said control signal causing said motor to revolve at an increased or decreased revolution rate in response to said sensed pressure, and when no pressure is sensed with said pressure sensing means, to revolve at a predetermined revolution rate including zero revolution,
   wherein said pressure sensing means comprises front and rear grip members which are made of relatively rigid synthetic resin and are coupled with each other to form centrally and along the entire length thereof a coupling conduit which communicates with said suction tip and said pumping tube, and to form around and outward said coupling conduit an empty space, said rear grip member having at the rear end and around said coupling conduit a cylindrical groove at the bottom of which said outlet is formed to communicate with said empty space, said front grip having an opening which communicates with said empty space and a resilient membrane being secured to said opening for transmission of the pressure exerted thereupon to said outlet, and
   wherein a double lumen pipe is used only at a portion adjacent said rear grip member in place of said pressure conduit and pumping tube and at the other portion remote from said rear grip member said pressure conduit and pumping tube are used, said double lumen pipe being inserted into said cylindrical groove so as to effect communication with said outlet and coupling conduit, one lumen of said double lumen pipe communicating with said outlet and pressure conduit and the other lumen communicating with said coupling conduit and pumping tube.

4. A blood suction device according to claim 3, wherein said one lumen of said double lumen communicating with said outlet has a stainless steel pipe inserted therein at the region where said cylindrical groove extends.

* * * * *